United States Patent [19]

DeGraw et al.

[11] Patent Number: 4,460,591
[45] Date of Patent: Jul. 17, 1984

[54] 8,10-DIDEAZAMINOPTERINS

[75] Inventors: Joseph I. DeGraw, Sunnyvale, Calif.; Lawrence F. Kelly, Canberra, Australia; Francis M. Sirotnak, New York, N.Y.

[73] Assignee: SRI International, Menlo Park, Calif.

[21] Appl. No.: 411,658

[22] Filed: Aug. 26, 1982

[51] Int. Cl.³ ............... C07D 471/04; C07D 487/04; A61K 31/505
[52] U.S. Cl. .................... 424/251; 544/260; 544/279
[58] Field of Search ............... 544/279; 424/251

[56] References Cited

FOREIGN PATENT DOCUMENTS 1534238 11/1978 United Kingdom ............ 544/260

OTHER PUBLICATIONS

J. I. DeGraw and F. M. Sirotnak, *Cancer Treatment Reports*, 62, 1047, (1978).
J. I. DeGraw, R. L. Kisliuk, Y. Gaumont and C. M. Baugh, *J. Med. Chem.*, 17, 470, (1974).
J. I. DeGraw, R. L. Kisliuk, V. H. Brown and Y. Gaumont, *Chem. Biol. Pteridines*, 6, 229, (1979).
A. Srinivasan and A. D. Broom, *J. Org. Chem.*, 46, 1777, (1981).

*Primary Examiner*—Donald G. Daus
*Assistant Examiner*—S. A. Gibson
*Attorney, Agent, or Firm*—Ciotti & Murashige

[57] ABSTRACT

8,10-Dideazaminopterins of the formula

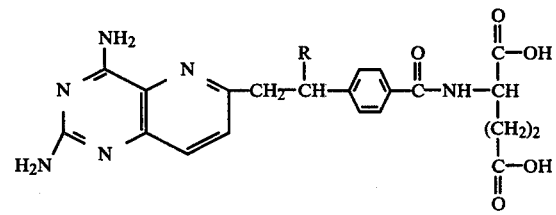

where R is hydrogen or alkyl of 1 to about 8 carbon atoms and their carboxylate and acid addition salts are described. These compounds exhibit antineoplastic activity that is similar to but more effective than methotrexate.

11 Claims, No Drawings

8,10-DIDEAZAMINOPTERINS

DESCRIPTION

1. Reference to Government Grant

The invention described herein was made in the course of work under grants from the National Institute of Health.

2. Technical Field

The invention is in the field of pterin chemistry and cancer therapy. More specifically it concerns 8,10-dideazaminopterin and its 10-alkyl analogs and their use as antineoplastic agents.

3. Background Art

Aminopterin and its N-10-methyl derivative, methotrexate, have long been recognized as powerful antineoplastic agents. Methotrexate has enjoyed some thirty years of acceptance as a clinically useful anti-cancer drug. The drugs are antimetabolites inhibiting dihydrofolate reductase (DHFR). They affect both neoplastic and normal host tissue.

J. I. DeGraw and F. M. Sirotnak, Cancer Treatment Reports, 62, 1047 (1978), British Pat. No. 1,534,238, dated Nov. 29, 1978 and U.S. application Ser. No. 75,913, filed Sept. 17, 1979 report that 10-deazaminopterin exhibited more potent antitumor activity than aminopterin and methotrexate in experimental tumors in mice. Specifically, it was found to have a wider spectrum of activity, better penetration of tumor tissue and more favorable distribution and kinetic parameters for tumor versus normal tissue. The cited U.S. patent application also teaches that antitumor effect and the spectrum of activity of 10-deazaminopterin were enhanced by incorporation of alkyl groups of short chain length at the 10 carbon atom.

Alterations of the pteridine ring of folic acid have also been investigated. The synthesis and antifolate activity of 8-deazafolic acid was reported by J. I. DeGraw, R. L. Kisliuk, Y. Gaumont and C. M. Baugh *J Med Chem*, 17, 470 (1974) and 8,10-dideazafolic acid was reported in J. I. DeGraw, R. L. Kisliuk, V. H. Brown and Y. Gaumont, *Chem Biol Pteridines*, 6, 229 (1979). Both of these compounds were active antifolates, but did not significantly affect DHFR. A. Srinivasan and A. D. Broom, *J Org Chem*, 46, 1777 (1981) reported the preparation of 8-deazaminopterin and 8-deazamethotrexate, but did not report biological activity for the compounds.

DISCLOSURE OF THE INVENTION

The compounds of the invention are 8,10-dideazaminopterins of the formula:

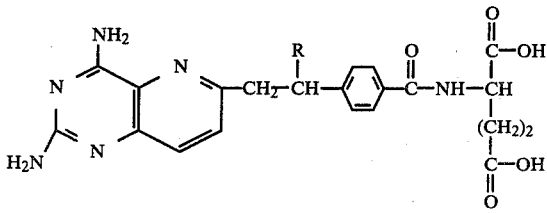

where R is H or alkyl of 1 to about 8 carbon atoms and pharmaceutically acceptable salts thereof.

Antineoplastic compositions containing the compounds of the above formula comprise a therapeutically effective amount of one or more of the compounds in combination with a pharmaceutically acceptable carrier. Living animals, including humans, are treated for cancer by administering therapeutically effective amounts of such compositions, typically in a unit parenteral dosage form, to the animal.

MODES FOR CARRYING OUT THE INVENTION

As indicated in the above formula the number 10 carbon atom of the invention compounds may be unsubstituted or substituted with an alkyl group of 1 to about 8 carbon atoms, preferably 1 to 4 carbon atoms. The alkyl substituent may be straight chain or branched chain. Exemplary alkyl groups include methyl, ethyl, propyl, isopropyl, butyl, isobutyl, sec-butyl, tert-butyl, amyl, iso-amyl, sec-amyl, tert-amyl, iso-hexyl, heptyl, iso-heptyl, octyl, iso-octyl, 2-ethylhexyl, and tert-octyl. Examples of 8,10-dideazaminopterins of the above formula are 8,10-dideazaminopterin, 10-methyl-8,10-dideazaminopterin, 10-ethyl-8,10-dideazaminopterin, 10-n-propyl-8,10-dideazaminopterin, 10-isopropyl-8,10-dideazaminopterin, 10-n-butyl-8,10-dideazaminopterin, 10-n-amyl-8,10-dideazaminopterin, 10-n-hexyl-8,10-dideazaminopterin, 10-n-heptyl-8,10-dideazaminopterin, and 10-n-octyl-8,10-dideazaminopterin.

The pharmaceutically acceptable salts of the above described 8,10-dideazaminopterins include acid addition salts and carboxylate salts. These salts are "pharmaceutically acceptable" in that they are nontoxic and functionally equivalent to the base compound(s). Acid addition salts are formed by reacting one or more of the free $NH_2$ groups of the 8,10-dideazaminopterins with an appropriate acid. Suitable acids include inorganic acids, for example, hydrochloric, hydrobromic, nitric, sulfuric or phosphoric acid; organic carboxylic acids such as glycolic, hydroxymaleic, malic, tartaric, citric, salicylic, o-acetyloxybenzoic, nicotinic and isonicotinic acid; and organic sulphonic acids such as methanesulfonic, ethanesulfonic, 2-hydroxyethane sulfonic, p-toluenesulfonic or naphthalene-2-sulfonic acid.

Carboxylate salts are formed by reacting a suitable base with one or more of the free carboxyl groups of the 8,10-dideazaminopterins. Suitable bases include alkali metal or alkaline earth metal hydroxides or carbonates, for example, sodium hydroxide, potassium hydroxide, calcium hydroxide, magnesium hydroxide and corresponding carbonates; and nitrogen bases such as ammonia and alkylamines such as trimethylamine, and triethylamine.

The compounds of this invention may be synthesized by one or more of three separate routes, designated Schemes A, B, and C herein.

The basic reaction sequence of scheme A is set forth below:

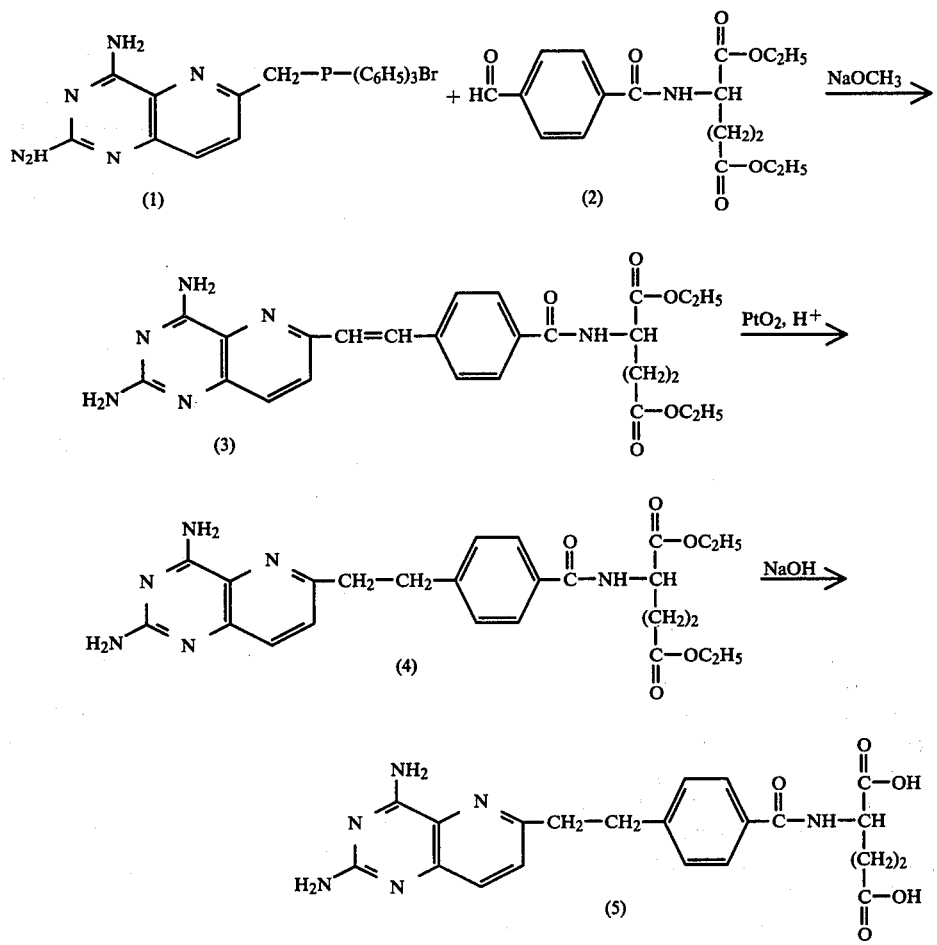

In scheme A 2,4-diamino-6-triphenylphosphoranylmethylpyrido[2,3-d]pyrimidinyl bromide (1) is condensed with the diethyl ester of p-formylbenzoyl-L-glutamate (2) in dimethylformamide as catalyzed by sodium methoxide to afford 8,10-dideza-9,10-dehydroaminopterin diethyl ester (3). Other bases capable of formation of the 6-triphenylphosphinylide of (1) may be employed along with other suitable polar organic solvents. The dehydro ester (3) is hydrogenated over platinum oxide in organic solvent or aqueous organic medium containing some acetic acid or other suitable acid. The resulting saturated ester (4) is saponified preferably with dilute alkali in the presence of a polar cosolvent such as 2-methoxyethanol to afford 8,10-deazaminopterin (5).

The reaction sequence of Scheme B is set forth below:

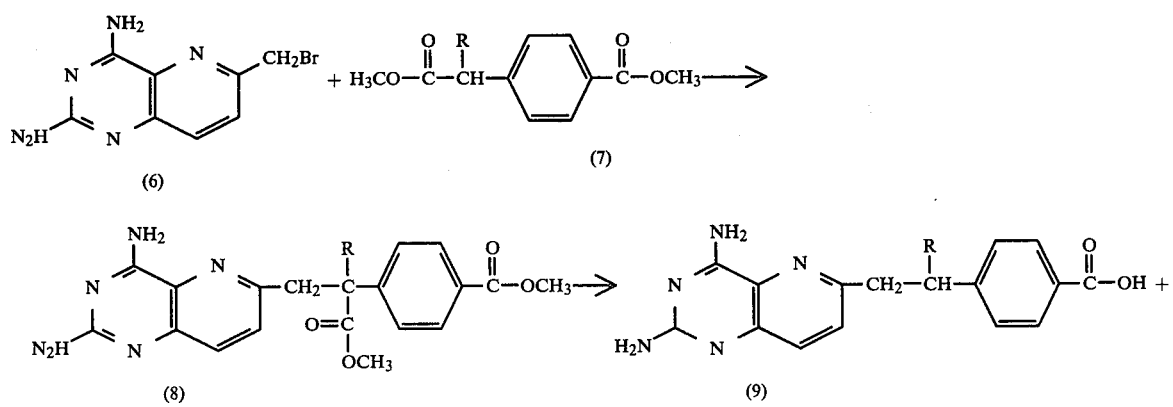

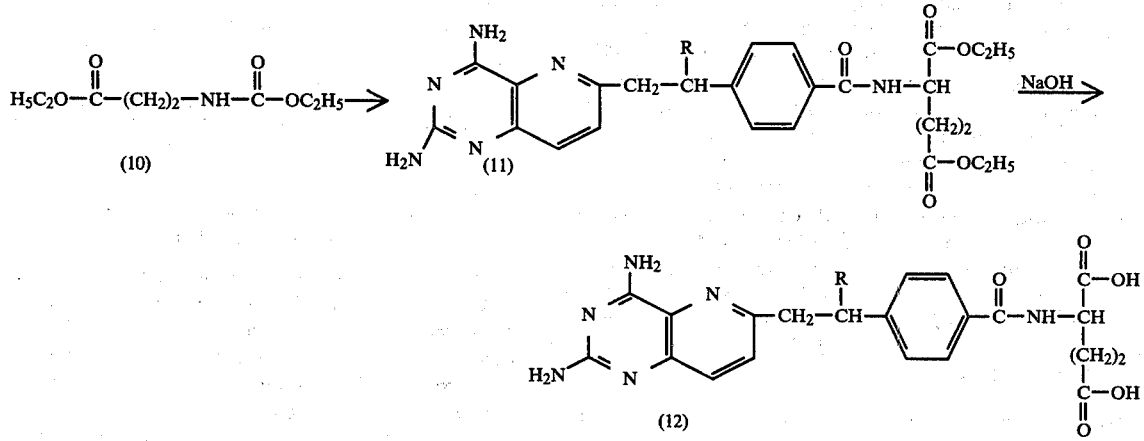

In scheme B the bromomethyl compound (6) is used to alkylate the anion of dimethyl homoterephthalate or an appropriately α-alkyl substituted homoterephthalate (7). Any common ester of homoterephthalate acid may be used and the anion may be generated by alkali hydrides, alkoxides, hydroxides and other bases obvious to one skilled in the art. A suitable polar organic solvent such as dimethyl formamide is employed. The 10-carboxylate compound (8) so obtained is treated in dimethyl sulfoxide or hexamethyl phosphoramide solvent with an alkali metal halide or cyanide to cause cleavage of the 10-carboxylate ester with subsequent decarboxylation of the 10-carboxylic acid to afford a 2,4-diamino pteroic acid intermediate (9). The useful temperature range for the process is 100°-200° C., preferably about 170°-180° C. The pteroic acid compound (9) is then coupled with diethyl L-glutamate (10). Activation of the benzoic carboxylate moiety is achieved via the mixed anhydride as generated in the presence of isobutyl chloroformate and triethyl amine. Other chloroformate esters along with other organic bases would be suitable for this purpose. The pteroyl glutamate diester (11) so obtained is hydrolyzed via treatment with an alkali hydroxide or carbonate in aqueous alcoholic medium, preferably aqueous 2-methoxyethanol to afford the respective 8,10-dideazaminopterin (12).

The reaction sequence for scheme C is as follows:

zoate (14) in the presence of a strong base such as sodium methoxide to yield a 9,10-dehydro pteroate ester (15). A variety of bases such as alkali hydrides, alkoxides, hydroxides or strong organic bases such as tertiary amines may be used to catalyze the condensation. Hydrogenation of the dehydro ester (15) in an aqueous or alcoholic medium containing acetic acid with subsequent hydrolysis affords the 2,4-diamino pteroic acid intermediate (9), which is convertible to the aminopterin as described above with respect to scheme B.

The use of these reaction schemes to prepare representative 8,10-dideazaminopterins of the invention is described in the following examples. These examples are not intended to limit the invention in any manner. In the examples reactants and products are designated by the same reference numerals are were used in the above descriptions of the reaction schemes.

EXAMPLE 1: Preparation of 8,10-Dideazaminopterin (5) by Scheme A

Step 1.
2,4-Diamino-6-bromomethylpyrido[2,3-d]pyrimidine Hydrobromide (6)

The triphenylphosphorane (1) was made from the bromomethyl compound (6) of scheme B. The bromomethyl compound was made as follows.

To a solution of 9.13 g (0.035 mole) of triphenylphos-

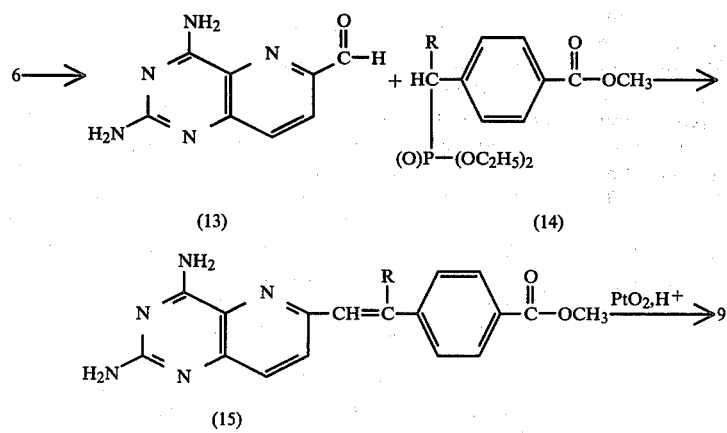

In scheme C the bromomethyl compound (6) is converted to the aldehyde (13) by treatment with the sodium salt of 2-nitropropane in methanol. The aldehyde is then condensed with a diethyl phosphonomethylbenphine in 70 ml of dimethylformamide at 5°-10° C. was slowly added 1.93 ml (0.035 mole) of bromine to form triphenylphosphine dibromide. The yellow-orange mixture was then treated with 1.91 g (0.01 mole) of 2,4-diamino-6-hydroxymethylpyrido[2,3-d]pyrimidine at 10° C. The mixture was stirred for 45 minutes at ambient temperature. The red solution was cooled to 10° C., treated with 1 ml of ethanol (dropwise) and stirred for an hour at ambient temperature. The solution was concentrated to a volume of 10 ml in vacuo and washed thrice with 90-ml portions of warm (40° C.) benzene. The residual liquid was treated with 30 ml of hot acetic acid. The hot solution was filtered and the filtrate chilled to afford 2.44 g of crystalline precipitate; UV $\lambda$ pH 1 248 nm ($\epsilon$ 20, 200), 320 (8,780), 333 (7,030); $\lambda$ pH 13 270 (11,050), 342 (6,300). Calc'd for $C_8H_8N_5Br.HBr$: C, 28.7; H, 2.7; N, 20.9; Br, 47.7. Found: C, 28.9; H, 2.85; N, 21.1; Br, 47.4.

Step 2. 8,10-Dideaza-8,10-dehydroaminopterin Diethyl Ester (3)

A mixture of 2.0 g (5.69 mmoles) of the bromomethyl compound (6), 1.56 g (5.95 mmole) of triphenylphosphine and 50 ml of dimethylformamide was stirred at 60° C. for 1.5 hours. The mixture containing the triphenylphosphorane (1) was cooled to room temperature and 2.1 g (6.27 mmoles) of diethyl p-formylbenzoyl-L-glutamate (2) was added followed by 0.62 g (11.5 mmoles) of sodium methoxide. The mixture was stirred for 24 hours at ambient temperature, filtered and the filtrate was evaporated in vacuo. Toluene (20 ml) was added and the mixture stirred at 40° C. until a homogeneous solid precipitate formed. Ether (30 ml) was added and the solid was collected by filtration and washed with 100 ml of ether. The dried material, 3.6 g, was dissolved in 15 ml of dimethyl formamide, filtered, and the filtrate was diluted with 100 ml of ice water, followed by refrigeration for 2 hours. The precipitate was collected, washed with water and ether and dried to afford 0.9 g; UV $\lambda$ pH 1 270 nm, 318, 255; $\lambda$ pH 11 290, 330, 370; NMR (DMSO-$d_6$), 1.05 (6H, m, ester $CH_3$), 1.8–2.5 (4H, m, —$CH_2CH_2$—), 3.6–4.4 (5H, m, —NHCH, ester —OCH$_2$—), 7.2–8.0 (10H, m, C-7, C-8 H's, —CH=CH—, $C_6H_4$, $NH_2$).

Step 3. 8,10-Dideazaminopterin Diethyl Ester (4)

A mixture of 0.9 g of the olefinic ester (3), 2250 mg of platinum oxide, 250 ml of ethanol and 50 ml of acetic acid was stirred for 24 hours under an atmosphere of hydrogen at which time the ultraviolet spectrum showed disappearance of the starting compound. The catalyst was removed by filtration and the filtrate evaporated in vacuo to leave a dark gum. The material was chromatographed on silica gel with successive elution by chloroform, chloroform-methanol (97:3) and chloroform-methanol (90:10) to afford 0.28 g of yellow solid; UV $\lambda$ pH 11 275 nm, 335, MS m/e 494; NMR (DMSO-$d_6$) $\delta$ 1.1 (6H, m, ester $CH_3$), 2.0 (2H, m, —CHCH$_2$ of glutamate), 3.08 (4H, br s, —CH$_2$CH$_2$—), 4.02 (4H, q, —OCH$_2$), 4.4 (1H, m, NH—CH), 6.08 (2H, s, $NH_2$), 7.5–7.8 (8H, m, $H_2N$+aromatic H's), 8.6 (1H, d, amide NH). Calc'd for $C_{25}H_{30}N_6O_5.\frac{1}{2}$ $H_2O$: C, 59.6; H, 6.21; N, 16.7. Found: C, 59.6; H, 6.20; N, 16.3.

Step 4. 8,10-Dideazaminopterin (5)

To a solution of 0.28 g of the diester (4) in 4 ml of 2-methoxyethanol was added 1.5 ml of 1N sodium hydroxide. The resulting solution was kept at room temperature for 4.5 hours, diluted with 10 ml of water and acidified with acetic acid to precipitate the product. The solid was collected, washed with water and dried to leave 0.21 g (82%) of pale yellow crystals; UV $\lambda$ pH 11 238 nm ($\epsilon$ 34,340), 276 (10,310), 344 (5,830). Calc'd for $C_{21}H_{22}N_6O_5.1\frac{3}{4}$ $H_2O$: C, 53.7; H, 5.43; N, 17.9. Found: C, 54.1; H, 5.41, N, 17.5.

EXAMPLE 2: Preparation of 8,10-Dideazaminopterin (5) by Scheme B

Step 1. 4-Amino-4-desoxy-10-carboxy-8,20-dideazapteroic Acid Dimethyl Ester (8)

To a stirred mixture of potassium hydride (0.69 g of 35% oil suspension, 6.0 mmole) in 5 ml of dry dimethylformamide at 0° C. was added 1.25 g (6.0 mmole) of dimethyl homoterephthalate (7) in 5 ml of dimethylformamide. After 30 minutes the red solution was coooled to −40° C. and 0.71 g (1.9 mmol) of the bromomethyl compound (6) in 10 ml of dimethylformamide was added over a 10 minute period with quenching of the red color. The mixture was brought to room temperature and stirred for 2 hours. The solvent was removed in vacuo and the residue was partitioned between 10 ml of chloroform and 5 ml of water. The mixture was filtered through a pad of celite, the filtrate and washings concentrated and the resultant solution was chromatographed on silica gel with elution by $CHCl_3$, then $MeOH$—$CHCl_3$ (1:6). The chloroform solution was dried over magnesium sulfate and evaporated in vacuo. The residue was treated with 15 ml of etherhexane (2:1). The supernatant was decanted and the insoluble gum was washed with 10 ml of ether followed by decantation. The residual material was dried to leave 0.60 g (83%), m/e 380 (M+).

Step 2. 4-Amino-4-desoxy-8,10-dideazapteroic Acid (9)

The dimethyl ester (8, 0.60 g, 0.0016 mol) and 0.20 g (0.004 mol) of sodium cyanide in 8 ml of dimethylsulfoxide were stirred at 175°–180° C. under an atmosphere of nitrogen. After 2.5 hours the mixture was cooled and the solvent removed by freeze-drying in vacuo. The residue was dissolved in 10 ml of water, filtered and the filtrate acidified with acetic acid. The precipitate was collected, washed with water and dried to yield 0.50 g (97%); m/e 309 (M+); NMR (DMSO-$d_6$) $\delta$ 3.13 (4H, S, —$CH_2CH_2$—), 7.40 (4H, m, C-7H, C-8H, benzoate 3′, 5′-H), 7.85 (2H, d, 2′, 6′-H's).

Step 3. 8,10-Dideazaminopterin (5)

A mixture of 387 mg (0.0012 mol) of the pteroic acid (9), 0.34 ml (0.0024 mol) of triethylamine and 10 ml of dimethylformamide was warmed to 90° C. with stirring until solution was obtained. The solution was cooled to 0° to 5° C. and treated dropwise with 0.31 ml (0.0024 mole) of isobutyl chloroformate. After 1.5 hours at 0° to 5° C. the mixture was treated with a mixture of 575 mg (0.0024 mol) of diethyl-glutamate hydrochloride, 0.34 ml (0.0024 mol) of triethylamine and 3 ml of dimethylformamide. The mixture was stirred for 2 hours in the ice bath and at room temperature for 24 hours. The solvent was removed in vacuo and the residue was stirred with 10 ml of 5% sodium bicarbonate and 10 ml of ether for 30 min. The mixture was filtered and the cake dissolved in chloroform and evaporated to leave 300 mg (51%) of the diester (4); the ester was chromatographically identical to material prepared as in Step 3, scheme A. It was hydrolyzed as in Step 4, scheme A, Example I, to give 8,10-dideazaminopterin.

EXAMPLE 3: Preparation of 8,10-Dideazaminopterin (5) by Scheme C

Step 1. 2,4-Diamino-6-formylpyrido[2,3-d]pyrimidine (13)

2-Nitropropane (0.27 g, 3 mmole) was added to a stirred solution of 0.16 g (3 mmole) of sodium methoxide in 10 ml of dry methanol at room temperature. After 20 minutes 0.33 g (1 mmole) of the bromomethyl compound (6) in 10 ml of methanol was added and the resulting solution was stirred at ambient temperature for 20 hours. The precipitated solid was collected by filtration, washed with methanol and dried to leave 0.13 g (66%); m/e 189; UV (pH 11) 230, 252 (sh), 272, 345. NMR ($d_6$-DMS)) 7.63 (1H, d, 7-H), 7.97 (1H, d, 8-H), 9.91 (1H, S, CHO).

Step 2. Methyl p-Diethylphosphonomethylbenzoate (14, R=H)

A mixture of 2.29 g (10 mmol) of methyl 4-bromomethyl benzoate and 1.66 g (10 mmol) of freshly distilled triethyl phosphite was heated at 150°–160° C. for 3 hours. Any unreacted phosphite was purged in vacuo and the residual phosphonate ester was suitable for use in the next step; m/e 286; NMR (CDCl$_3$) 1.25 (6H, t, OCH$_2$CH$_3$), 3.20 (2H, d, J=22 Hz, CH$_2$P), 3.93 (3H, s, OCH$_3$), 4.05 (4H, q, OCH$_2$), 7.40 (2H, d, 3,5-H's), 8.05 (2H, d, 2,6-H's).

Step 3. Methyl 4-Amino-4-desoxy-9,10-dehydro-8,10-dideazapteroate (15, R=H)

A mixture of 100 mg (0.53 mmol) of the aldehyde (13), 165 mg (0.58 mmol) of methyl p-diethylphosphonomethylbenzoate (14), 62 mg (1.14 mmol) of sodium methoxide and 20 ml of dry dimethylformamide was stirred for 2 hours at 50° C. The solution was cooled, filtered and the filtrate evaporated in vacuo to leave a yellow solid. The material was recrystallized from 5% dimethylformamide in water to afford 95 mg (56%); m/e 321; UV (pH 1) 262, 318, 330, 335, (pH 11) 278, 328, 370; NMR ($d^6$-DMSO) 3.87 (3H, s, OCH$_3$), 7.90 (2H, d, J=17.6 Hz, trans olefin), other olefin proton as part of multiplet at 7.50.

Step 4. 4-Amino-4-desoxy-8,10-dideazapteroic Acid (9)

A mixture of 80 mg of the dehydro ester (15), 50 mg of platinum oxide and 10 ml of methanol containing 1 ml of acetic acid was stirred under an atmosphere of hydrogen for 2 hours. The catalyst was removed by filtration and the solvent evaporated in vacuo to leave 75 mg of the reduced ester, m/e 323 (M+). The reduced ester was dissolved in 2 ml of 2-methoxyethanol, treated with 1.0 ml of 1N sodium hydroxide and allowed to stand at ambient temperature for 3 hours. The solution was diluted with 10 ml of water, acidified with acetic acid and the precipitate collected to yield 30 mg (39%) of (9).

EXAMPLE 4: Preparation of 10-Methyl-8,10,dideazaminopterin (12, R=CH$_3$) by Scheme B

Step 1. Dimethyl α-Methylhomoterephthalate (7, R=CH$_3$)

A solution of dimethyl homoterephthalate (7, R=H) (4.16 g, 20 mmole) in 15 ml of dry tetrahydrofuran was added dropwise over 15 minutes to a stirred mixture of potassium hydride (2.5 g of 35% oil suspension, 22 mmole) in 75 ml of dry tetrahydrofuran at 0° C. After 30 minutes a homogeneous yellow suspension had formed. Methyl iodide (2.79 g, 22 mmole) was then added over a 5 minute period and the resulting mixture stirred for 30 minutes. The mixture was quenched with 2 ml of 50% acetic acid, diluted with 500 ml of water and extracted with ether. The ether extract was washed with water, dried over magnesium sulfate and evaporated to leave an oil. The material was chromatographed on silica gel with elution by ether-hexane (1:9) to afford (71%) of a clear oil; m/e 222 (M+); NMR (CDCl$_3$) 1.50 (3H, d, CH$_3$), 3.65 (3H, s, OCH$_3$), 3.93 (3H, s, OCH$_3$ benzoate).

Step 2. 4-Amino-4-desoxy-10-carboxy-10-methyl-8,10-dideazapteroic Acid Dimethyl Ester (8, R=CH$_3$)

The procedure described in Example 2, Step 1 was carried out except that dimethyl α-methyl-homoterephthalate was reacted with bromomethyl compound (6). The product diester was obtained as a yellow solid in 85% yield; m/e 395 (M+).

Anal Calc'd for $C_{22}H_{21}N_5O_4 \cdot H_2O$: C, 58.1; H, 5.61; N, 16.9. Found: C, 58.4; H, 5.30; N, 17.0.

Step 3. 4-Amino-4-desoxy-10-methyl-8,10-dideazapteroic Acid (9, R=CH$_3$)

The dimethyl ester (8, R=CH$_3$) was decarboxylated as in Example 2, Step 2 to afford the 10-methyl product as a yellow solid in 73% yield; m/e 323 (M+), NMR ($d^6$-DMSO) 1.23 (3H, d, CH$_3$), 3.06 (2H, m, 9-CH$_2$), 3.50 (1H, m, 10-H), 7.27 1H, d, 7-H), 7.39 (3H, m, 8-H, benzoate 3',5'-H's), 7.82 (2H, d, 2',6'H's).

Step 4. 10-Methyl-8,10-dideazaminopterin (12, CH$_3$)

The pteroic acid (9, R=CH$_3$) was coupled with diethyl L-glutamate (10) in the manner described in Example 2, Step 3. The ester (11, R=CH$_3$) was obtained in 20% yield. Thin layer chromatography (TLC) on silica gel (CHCl$_3$—CH$_3$OH, 9:1) showed a single spot, R$_f$ 0.4; m/e 508 (M+).

The ester was hydrolyzed as in Examples 1 and 2, to afford the product.

EXAMPLE 5: Preparation of 10-Propyl-8,10-dideazaminopterin (12, R=C$_3$H$_7$) by Scheme B

Step 1. Dimethyl α-Propylhomoterephthalate (7, R=C$_3$H$_7$)

Dimethyl homoterephthalate (7, R=H) was alkylated as in Example 4, Step 1 but with propyl bromide to afford the α-propyl product in 74% yield as an oil, m/e 250 (M+); NMR (CDCl$_3$) 0.91 (3H, t, CH$_3$), 1.26 (2H, m, —CH$_2$CH$_3$), 1.75–2.05 (2H, m, —CH$_2$C$_2$H$_5$), 3.62 (1H, t, —CH—C$_3$H$_7$), 3.66 (3H, s, OHC$_3$) 3.91 (3H, s, benzoate OCH$_3$).

Step 2. 4-Amino-4-desoxy-10-carboxy-10-propyl-8,10-dideazapteroic Acid Dimethyl Ester (8, R=C$_3$H$_7$)

The procedure described in Example 4, Step 1 was carried out except that dimethyl α-propylhomoterephthalate was reacted with the bromomethyl compound (6). The product diester was obtained as a yellow solid in 45% yield; m/e 423 (M+); NMR ($d^6$-DMSO) 0.72 (3H, t, CH$_3$), 1.05 (2H, m, —CH$_2$CH$_3$), 1.92 (2H, m, —CH$_2$C—COOMe) 3.57 (3H, s, COOCH$_3$), 3.63 (2H, m, 9-H's), 3.85 (3H, s, benzoate COOCH$_3$).

Step 3.
4-Amino-4-desoxy-10-propyl-8,10-dideazaminopteroic Acid (9, R=C$_3$H$_7$)

The dimethyl ester (8, R=C$_3$H$_7$) was decarboxylated as in Example 4, to give the 10-propyl product as a yellow solid in 81% yield, m/e 351 (M+); NMR (d$^6$-DMSO) 0.82 (3H, t, CH$_3$), 1.15 (2H, m, CH$_2$, CH$_3$), 1.63 (2H, m, —CH$_2$CH), 3.1 (2H, m, 9-CH$_2$), 3.5 (1H, m, 10-H), 7.20 (1H, d, 7-H), 7.31 (1H, d, 8-H), 7.36 (2H, d, 3',5'-H's), 7.79 (2H, d, 2',6'-H's).

Step 4. 10-Propyl-8,10-dideazaminopterin (12, R=C$_3$H$_7$)

The pteroic acid (9, R=C$_3$H$_7$) was condensed with diethyl L-glutamate in the manner described in Example 4, Step 3. The crude ester (11, R=C$_3$H$_7$) was obtained in 38% yield; TLC (CHCl$_3$—MeOH, 9:1) R$_f$ 0.40; m/e 536 (M+). The ester was saponified as in Example 4, to give the product 12 in 53% yield, m/e for the tetratrimethylsilyl derivative, 768 (M+).

EXAMPLE 6: Preparation of 10-Amyl-8,10-dideazaminopterin (12, R=C$_5$H$_{11}$) by Scheme B

Step 1. Dimethyl α-Amylhomoterephthalate (7, R=C$_5$H$_{11}$)

Dimethyl homoterephthalate (7, R=H) was alkylated as in Example 4, Step 1, but with n-amyl bromide to give the α-amyl product in 72% yield as an oil after chromatography on silica gel; m/e 278 (M+); NMR (CDCl$_3$) 0.84 (3H, t, CH$_3$), 1.25 (6H, m, —CH$_2$CH$_2$CH$_2$—), 1.77-2.07 (2H, m, —CHCH$_2$—), 3.60 (1H, t, —CH— C$_5$H$_{11}$), 3.66 (3H, s, OCH$_3$), 3.91 (3H, s, benzoate OCH$_3$).

Step 2.
4-Amino-4-desoxy-10-carboxy-10-amyl-8,10-dideazapteroic Acid Dimethyl Ester (8, R=C$_5$H$_{11}$)

The procedure described in Example 4, Step 1 was carried out except that dimethyl α-amyl-homoterephthalate was reacted with the bromomethyl compound (6). The product was obtained as a yellow solid in 29% yield, m/e 451 (M+); NMR (d$^6$-DMSO) 0.71 (3H, t, CH$_3$), 0.95-1.30 (6H, m, —CH$_2$CH$_2$CH$_2$—), 1.92 (2H, m, —CH$_2$—C—COOCH$_3$) 3.57 (3H, s, COOCH$_3$), 3.63 (2H, m, 9-H's), 3.85 (3H, s, benzoate COOCH$_3$).

Step 3. 4-Amino-4-desoxy-10-amyl-8,10-dideazapteroic Acid (9, R=C$_5$H$_{11}$)

The dimethyl ester (8, R=C$_5$H$_{11}$) was decarboxylated as in Example 4, Step 2 to give the 10-amyl product as a yellow solid in 58% yield; m/e 379 (M+).

Step 4. 10-Amyl-8,10-dideazaminopterin (12, R=C$_5$H$_{11}$)

The pteroic acid (9, R=C$_5$H$_{11}$) was coupled with diethyl L-glutamate in the manner described in Example 4. The crude ester (11, R=C$_5$H$_{11}$) was obtained and was chromatographed on silica gel with elution by chloroform-methanol, 19:1; m/e 564 (M+). The purified ester was saponified as in Example 4, to give the product in 60% yield; m/e for the tetratrimethylsilyl derivative 796 (M+).

The physical properties of the 8,10-dideazaminopterins of the invention are similar to methotrexate. Accordingly they may be formulated for use as antineoplastic agents in a manner similar to methotrexate. Such formulations will comprise the 8,10-dideazaminopterins dissolved/suspended in pharmaceutically acceptable liquid carrier such as mineral oil or saline or mixed with pharmaceutically acceptable solid carriers such as talc, magnesium sterate, starches, and sugar, and if desired, formed into dosage forms such as tablets, cachets, suppositories and capsules. As used to describe such carriers the term "pharmaceutically acceptable" means that the carrier is nontoxic, generally inert, and does not affect the functionality of the active ingredient(s) adversely. The term carrier includes materials that are sometimes referred to as diluents or vehicles in the pharmaceutical formulation art. The 8,10-dideazaminopterins will mainly be used as aqueous solutions of their sodium salts for administration intravenously or subcutaneously.

The dose and the dosage regimen will depend upon the cancer being treated, the mode of administration, the animal species involved, and the weight of the patient. The dosage will typically range between about 0.1 to 500 mg/day. Treatment will typically be given daily until the cancer is in remission. Maintenance treatments during remission will typically be made on an intermittent basis.

The compounds may be administered parenterally (e.g. intravenous, intraarterial, intraperitoneal, intramuscular, intrathecally, subcutaneously) or orally. They are effective in treating leukemias, lymphomas, and solid cancers such as chloriocarcinoma, hydatidiform mole, chlorioadenoma destruens, acute lymphocytic leukemia, mycosis fungoides, osteogenic sarcoma, lymphosarcoma and other non-Hodgkin's lymphomas, breast tumors, bronchogenic carcinomas, tumors of the testis, and Burkitt's lymphoma. They may be administered with other drugs such as chlorambucil. When administered locally to treat a regionalized neoplasm, counteragents such as folinic acid may be given systemically to counteract the systemic activity of the 8,10-dideazaminopterin.

The 8,10-dideazaminopterins are in the class of antineoplastic agents designated antimetabolites. Like methotrexate, they bind tightly to DHFR and prevent the enzyme from activating the conversion of dihydrofolate to tetrahydrofolate. The blockage of this pathway inhibits DNA synthesis thereby inhibiting cancer reproduction of cancerous cells. Accordingly, as used herein the term "therapeutically effective amount" means a quantity of one or more of the invention compounds that, when administered to a patient inhibits neoplastic growth. The compounds of the invention thus function similarly to methotrexate in cancer therapy but have enhanced antitumor potency and spectrum of activity as compared to methotrexate.

The effectiveness of the invention compounds as antineoplastic agents may be demonstrated by subjecting them to the L-1210 murine leukemia assay. This is a standard assay that is used to evaluate the efficacy of compounds as antineoplastic agents for treating humans. The assay is described by D. J. Hutchinson, D. C. Robinson, D. Martin, O. L. Ittenson and Dillenberg, *Journal Cancer Research,* 22 57–72 (1962). It is a procedure for evaluating a compound for increase in median life span in treated animals and untreated controls both infected with L-1210 leukemia cells. The test compound is dissolved in 0.2 ml of 0.1N sodium hydroxide, adjusted to pH 7, and the solution diluted to 10 ml with distilled water. Mice are injected once per day every other day for a total of 5 injections starting one day after transplantation of $10^6$ tumor cells/mouse. The results of this assay on the 8,10-dideazaminopterins of the Examples were as follows:

| Compound | Dosage (mg/kg) | Increase life Span (%) |
|---|---|---|
| Examples 1-3 | 0.75 | 189 |
| Example 5 | 6 | 176 |
| Methotrexate | 12 | 163 |
| Control | — | 0 |

It is apparent from the above results that the life spans of the mice were increased considerably by administration of the invention compounds.

Modifications of the above described modes for carrying out the invention that are obvious to those of skill in organic chemistry synthesis, pharmaceutical formulation, cancer therapy, and/or related fields are intended to be within the scope of the following claims.

We claim:

1. A compound of the formula

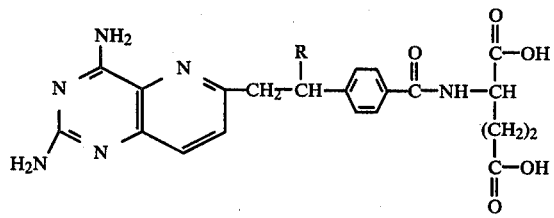

where R is a hydrogen or alkyl of 1 to about 8 carbon atoms, and pharmaceutically acceptable salts thereof.

2. The compound of claim 1 wherein R is hydrogen, methyl, propyl, or amyl.

3. The compound of claim 1 wherein said pharmaceutically acceptable salts are sodium salts.

4. 8,10-dideazaminopterin.

5. 10-Methyl-8,10-dideazaminopterin.

6. 10-Propyl-8,10-dideazaminopterin.

7. 10-Amyl-8,10-dideazaminopterin.

8. An antineoplastic composition comprising a therapeutically effective amount of the compound of claim 1, 2, 3, 4, 5, 6, or 7 combined with a pharmaceutically acceptable carrier.

9. An antineoplastic composition for parenteral administration comprising a therapeutically effective amount of a sodium salt of the compound of claim 1, 2, 4, 5, 6, or 7 dissolved in a pharmaceutically acceptable aqueous solvent.

10. A method of inhibiting neoplastic growth in a living animal comprising administering a therapeutically effective amount of the compound of claim 1, 2, 3, 4, 5, 6, or 7 to the animal.

11. A method of inhibiting neoplastic growth in a living animal comprising administering a therapeutically effective amount of an aqueous solution of a sodium salt of the compound of claim 1, 2, 4, 5, 6, or 7 to the animal intravenously or subcutaneously.

* * * * *